United States Patent [19]
Fischer et al.

[11] Patent Number: 5,992,235
[45] Date of Patent: Nov. 30, 1999

[54] ULTRASONIC TEST HEAD AND METHOD FOR ITS OPERATION

[75] Inventors: Eberhard Fischer, Röttenbach; Werner Rathgeb, Erlangen; Anton Erhard, Berlin; Walter Möhrle, Berlin; Hermann Wüstenberg, Berlin, all of Germany

[73] Assignee: Siemens Aktiengesellschaft, Munich, Germany

[21] Appl. No.: 08/433,155

[22] Filed: May 3, 1995

Related U.S. Application Data

[63] Continuation of application No. PCT/EP93/03069, Nov. 2, 1993.

[30] Foreign Application Priority Data

Nov. 3, 1992 [DE] Germany .................. 92 14 948 U

[51] Int. Cl.⁶ .................. G01N 29/06; G01N 29/10; G01N 29/24
[52] U.S. Cl. .............. 73/617; 73/622; 73/624; 73/628; 73/626
[58] Field of Search ............ 73/628, 625, 626, 73/644, 622, 617, 620, 624, 627

[56] References Cited

U.S. PATENT DOCUMENTS

| | | | |
|---|---|---|---|
| 2,700,895 | 2/1955 | Carson | 73/626 |
| 2,784,325 | 3/1957 | Halliday et al. | 73/628 |
| 2,875,607 | 3/1959 | Boxcer et al. | 73/628 |
| 4,275,598 | 6/1981 | Engl | 73/622 |
| 4,458,534 | 7/1984 | Kising | 73/642 |
| 4,481,822 | 11/1984 | Kubota et al. | 73/625 |
| 4,497,210 | 2/1985 | Uchida et al. | . |
| 4,712,428 | 12/1987 | Ishii et al. | 73/644 |
| 4,821,575 | 4/1989 | Fujikake et al. | . |
| 4,831,601 | 5/1989 | Breimesser et al. | 73/626 |

FOREIGN PATENT DOCUMENTS 0105966  4/1984  European Pat. Off. .

OTHER PUBLICATIONS

Patent Abstracts of Japan, vol. 10, No. 198, Jul. 11, 1986: & JP-A-84-0162336 (Sasaki) Jul. 31, 1984.

Materialprüfung 28, 1986, No. 1/2, Jan./Feb. (Wüstenberg et al.), pp. 20-24.

*Primary Examiner*—Hezron E. Williams
*Assistant Examiner*—Rose M. Miller
*Attorney, Agent, or Firm*—Herbert L. Lerner; Laurence A. Greenberg

[57] ABSTRACT

An ultrasonic test head for ultrasonically testing flaws in a workpiece includes a common housing. An ultrasonic transducer configuration is disposed in the common housing. At least one ultrasonic transducer array is disposed in the common housing for operation in a pulse echo mode for transverse waves propagating in a workpiece. The ultrasonic transducer configuration includes at least two acoustically separate ultrasonic transducers to be operated in a transmit/receive mode for longitudinal waves propagating near a surface in the workpiece. In a method for operating the ultrasonic test head, each ultrasonic transducer array or arrays is operated in a transmit/receive mode.

13 Claims, 4 Drawing Sheets

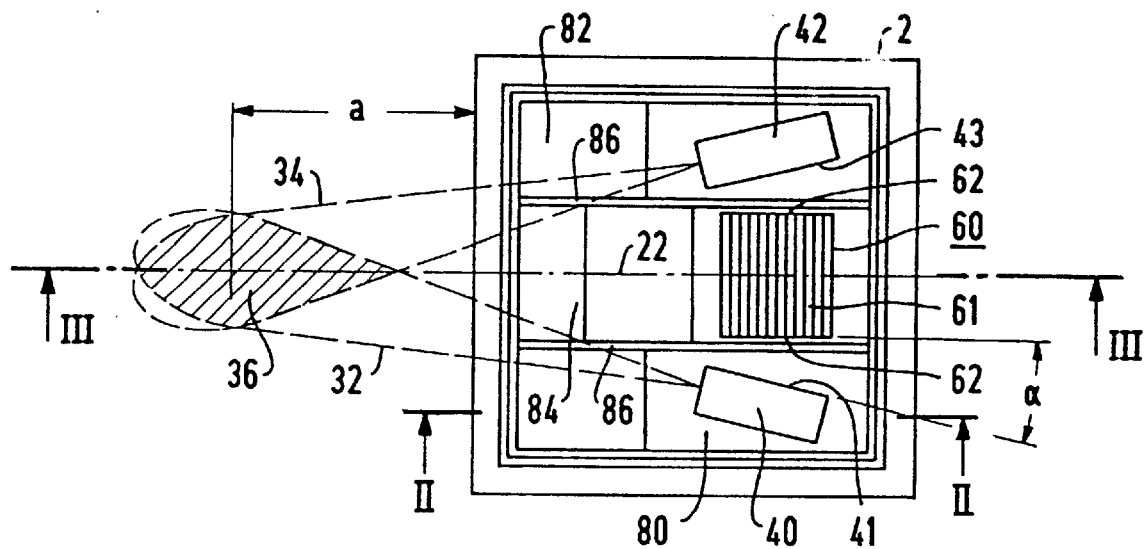
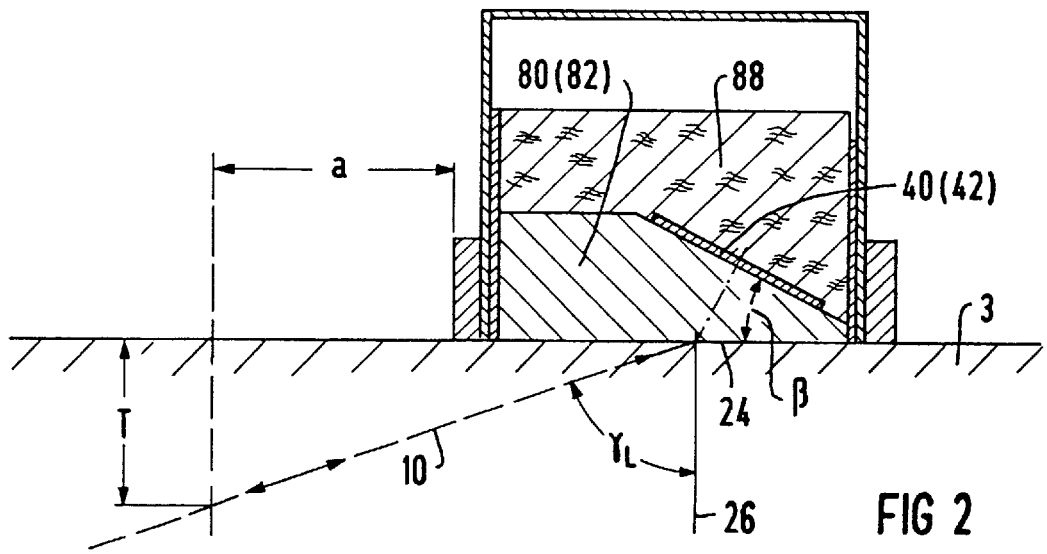

ULTRASONIC TEST HEAD AND METHOD FOR ITS OPERATION

CROSS-REFERENCE TO RELATED APPLICATION

This application is a Continuation of International Application Serial No. PCT/EP93/03069, filed Nov. 2, 1993.

BACKGROUND OF THE INVENTION

1. Field of the Invention

The invention relates to an ultrasonic test head for testing flaws in a workpiece, and to a method for its operation.

Crack-type flaws in a workpiece can have a varying depth and a varying orientation relative to the surface of the workpiece. In order to enable detection of all of the possible flaws in non-destructive ultrasonic testing, it is necessary to use a plurality of ultrasonic test heads, each of which is suitable for different types of flaws, and those ultrasonic test heads must be employed in successive measurements.

Test heads which are known from the publication entitled: "Materialprüfung 28"[Materials Testing 28] 1986, pp. 20–24, each contain two ultrasonic transducer arrays operated in the transmit/receive mode. Those ultrasonic transducer arrays are coupled to wedge attachments that are replaceable in a manner adapted to the particular testing problem involved.

Although with those known configurations high flexibility with respect to the direction at which sound enters can be attained, nevertheless different test heads must be used, in order to fit the depth of the flaw. The replacement of the test heads or prism wedges and the attendant necessity of repeating the measurements several times by passing over the entire testing zone again is time-consuming and should be avoided, especially in surroundings that can cause radiation exposure to the workers doing the testing. Additionally, correlating the results of tests obtained in the various measurements is more difficult.

SUMMARY OF THE INVENTION

It is accordingly an object of the invention to provide an ultrasonic test head for ultrasonic testing of flaws in a workpiece and a method for its operation, which overcome the hereinafore-mentioned disadvantages of the heretofore-known devices and methods of this general type and which permit a number of differently oriented flaws located at different depths to be detected without changing test heads.

With the foregoing and other objects in view there is provided, in accordance with the invention, an ultrasonic test head for ultrasonically testing flaws in a workpiece, comprising a common housing; an ultrasonic transducer configuration disposed in the common housing; and at least one ultrasonic transducer array being disposed in the common housing for operation in a pulse echo mode for transverse waves propagating in a workpiece; the ultrasonic transducer configuration including at least two acoustically separate ultrasonic transducers to be operated in a transmit/receive mode for longitudinal waves propagating near a surface in the workpiece.

The invention is based on the concept that a spatial separation between the ultrasonic transducers intended for transmission and those intended for reception, or in other words an operation of the ultrasonic transducer configuration in the transmit/receive mode, is necessary only whenever flaws that are located directly below the surface of the workpiece are to be demonstrated. An ultrasonic transducer configuration operated in the pulse echo mode, or in other words in which the ultrasonic transducers that are active for transmission are also active as receivers after the transmission, is not suitable for detecting flaws near the surface, since in that kind of operation there will always be a time slot following the transmission process in which the ultrasonic transducer configuration is practically blind to the signals being reflected back from the flaw, because of so-called after-ringing. Such after-ringing is caused by internal reflections in the test head, which are received by the ultrasonic transducers and are superimposed on the signals reflected back from the zone near the surface, and make the signals difficult to detect. The after-ringing is suppressed and flaws near the surface can be detected, by distributing the transmission function and the reception function to different ultrasonic transducers. This kind of spatial separation is not necessary in order to detect flaws near the surface, since the echo signals from greater depths do not arrive until the interference from internal reflection in the test head has largely faded. The flaws far from the surface can then be detected for different depth regions by means of an ultrasonic transducer array being operated in the pulse echo mode, which couples transversal waves into the workpiece, having a direction of propagation which can be controlled electronically in its azimuth, preferably in the angular range between 45° and 60°, by suitable phase-controlled triggering of the various transducer elements.

In accordance with another feature of the invention, the ultrasonic transducer array is disposed next to an ultrasonic transducer that can be operated as a transmitter and receiver for longitudinal waves.

In accordance with a further feature of the invention, the ultrasonic transducer array is disposed between two ultrasonic transducers that can be operated as transmitters and receivers for longitudinal waves.

In accordance with an added feature of the invention, these ultrasonic transducers are likewise constructed as an array.

As a result, the longitudinal waves coupled into the workpiece can additionally be pivoted laterally.

In accordance with an additional feature of the invention, the ultrasonic transducers disposed next to the ultrasonic transducer array have a rectangular reception or transmission surface and are disposed with their long edge obliquely relative to the long edge of the ultrasonic transducer array, in particular they are disposed in such a way that their long edges form an acute angle with one another.

In accordance with yet another feature of the invention, the ultrasonic test head additionally includes an ultrasonic transducer disposed with its transmission or reception surface parallel to the coupling surface.

With the objects of the invention in view, there is also provided a method for operating an ultrasonic test head, which comprises operating each of the ultrasonic transducer array or arrays in a transmit/receive mode.

In accordance with a concomitant mode of the invention, two spatially separate subgroups having a plurality of ultrasonic transducer elements are formed, and are separated from one another in particular by a subgroup formed of inactive ultrasonic transducer elements.

Other features which are considered as characteristic for the invention are set forth in the appended claims.

Although the invention is illustrated and described herein as embodied in an ultrasonic test head and a method for its operation, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 1 is a diagrammatic plan view of a test head according to the invention;

FIGS. 2 and 3 are longitudinal-sectional views of the test head of the invention which are taken along respective section lines II—II and III—III of FIG. 1, in the direction of the arrows;

DESCRIPTION OF THE PREFERRED EMBODIMENTS

Figure 3:
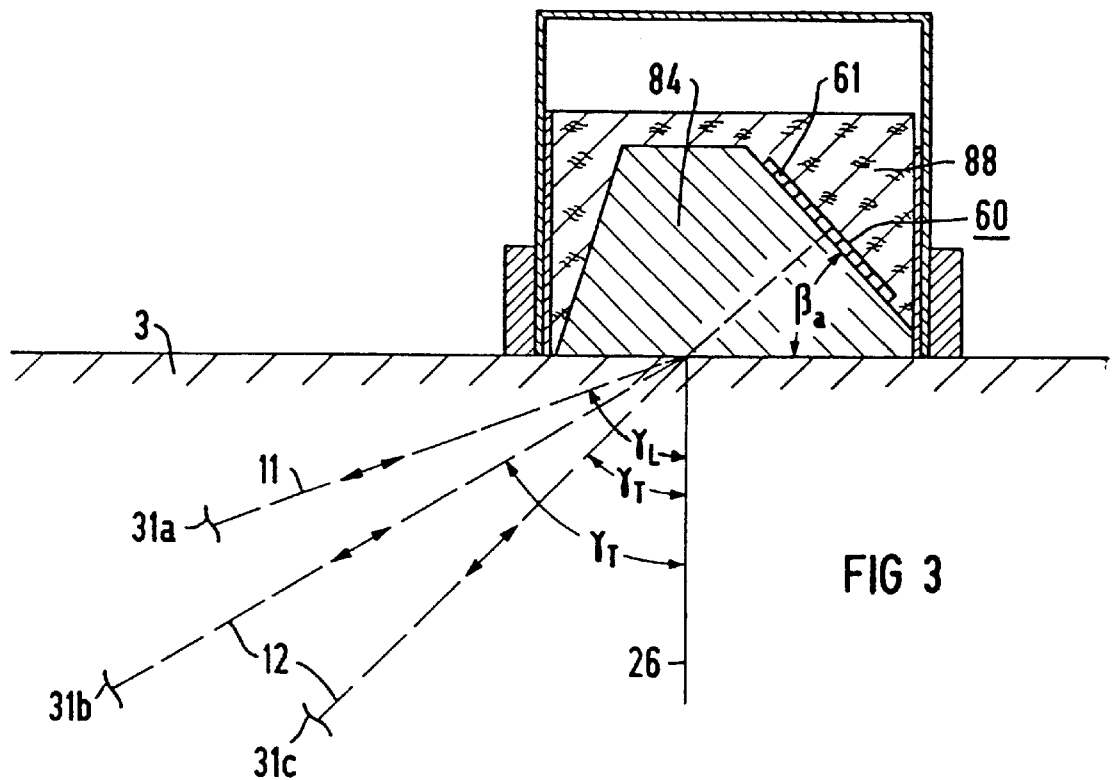

Referring now to the figures of the drawing in detail and first, particularly, to the plan view of FIG. 1 thereof, there is seen a housing 2 having a rectangular outline, in which an ultrasonic test head is disposed. The ultrasonic test head contains two eccentrically disposed piezoceramic ultrasonic transducers 40 and 42, each of which can be operated as both a receiver and as a transmitter for longitudinal waves that are propagated near the surface in a workpiece that is not shown in detail in the drawing. A linear ultrasonic transducer array 60 which is also disposed in this housing 2 between the two ultrasonic transducers 40 and 42, by way of example contains 12 individual ultrasonic transducer elements 61. The ultrasonic transducer array 60 is placed in the housing 2 with long edges 62 thereof oriented parallel to side walls of the housing and symmetrical with a center plane 22.

Through the use of delayed-transit-time triggering of the individual ultrasonic transducer elements 61, which are likewise formed of a piezoceramic, ultrasonic waves (longitudinal and transverse waves) can be coupled into the workpiece at different angles relative to the surface normal. Through the use of this azimuthal pivoting performed in the center plane 22, flaws located at different depths and positions in the workpiece can be detected without moving the test head.

The ultrasonic transducers 40 and 42 and the ultrasonic transducer array 60 are disposed on respective acoustically separate wedge-like delay bodies 80, 82 and 84, which by way of example are formed of polymethylmethacrylate or PMMA. In the exemplary embodiment of the drawing, the delay bodies 80 and 82 are provided with wedge surfaces that are parallel to one another, so that the transmitting and receiving surfaces of the ultrasonic transducers 40 and 42 disposed on these wedge surfaces are located in the same plane.

The delay bodies 80 and 84 on one hand, and the delay bodies 82 and 84 on the other hand, are acoustically separated from one another by an intermediate layer 86, for instance made of cork, in order to prevent direct crosstalk between the ultrasonic transducers 40 and 42 on one hand and the ultrasonic transducer array 60 on the other hand.

Each of the ultrasonic transducers 40 and 42 are individual transducers with a rectangular receiving and transmitting surface, and are disposed with respective long edges 41 and 43 thereof at an angle a that is oblique to the long edge 62 of the linear ultrasonic transducer array 60, in such a way that their long edges 41 and 43 are inclined to one another at an acute angle $2\alpha$.

Sound lobes 32 and 34 that originate at the receiving and transmitting surfaces of the respective ultrasonic transducers 40 and 42 are superimposed on one another below the plane of the drawing in a shaded region marked by reference numeral 36, the center of which is spaced apart laterally by a distance a from the housing 2. For the sake of simplicity, the diffraction of the sound lobes 32 and 34 that occurs at the surface of the workpiece is not shown in the drawing. This spacing a is equivalent to the distance of the focal region from the housing 2 within which there is maximum sensitivity of the transducer configuration. This is so if in one alternative, one of the ultrasonic transducers 40 and 42 is operated in the transmission mode and the other of the ultrasonic transducers 42 or 40 in the reception mode, or in another alternative, the ultrasonic transducer array 60 is operated in the transmission mode and the two ultrasonic transducers 40 and 42 are operated in the reception mode.

The lateral spacing a of the focal region is additionally determined by the geometric configuration of the ultrasonic transducers 40 and 42 in the housing and additionally, depending on the transmission/reception combination chosen, by the configuration and triggering of the ultrasonic transducer arrays, and can be adapted to the particular test requirements at hand.

In order to provide optimal superposition of the sound lobes 32 and 34, the wedge surfaces of the delay bodies 80 and 82 can moreover be constructed in such a way that the transmission and reception surfaces of the respective ultrasonic transducers 40 and 42 are also inclined relative to one another at an apex angle.

In the sectional view of FIG. 2 it can be seen that the ultrasonic transducers 40 and 42 are inclined by a wedge angle $\beta$ relative to a coupling surface 24. The wedge angle $\beta$ is selected in such a way that the ultrasonic transducers 40 and 42 are suitable for transmitting or receiving longitudinal waves 10 that are propagated in a workpiece 3 at an angle $\gamma_L$ of approximately 70° to a surface normal 26 and obliquely to the plane of the drawing. This wedge angle $\beta$ amounts to approximately 26.5°. The propagation direction $\gamma_L$ of the longitudinal waves 10 is defined by the wedge angle $\beta$ and the acoustical impedances of the delay body 80 or 82 and of the workpiece 3. A depth T and the lateral spacing a of the focal region located below the plane of the drawing, are influenced by the apex angle of the wedge surface and by the angle of inclination a seen in FIG. 1.

The ultrasonic transducers 40 and 42 are additionally embedded in a damping composition 88 that, for instance, is formed of a mixture of glue, rubber and ceramic, and are placed on the delay bodies 80 or 82 through $\gamma/4$ adaptation layers.

The sectional view of FIG. 3 shows that the linear ultrasonic transducer array 60 is disposed on a delay body 84 having a wedge angle $\beta_a$ which is larger than the wedge angle $\beta$ and amounts to approximately 46.5°. The ultrasonic transducer array 60 can be triggered in such a way that it can both transmit and receive transverse waves 12 that are propagated at an angle $\gamma_T$ of between 45° and 60° to the surface normal 26 in the workpiece 3 and can also transmit and receive longitudinal waves 11 that propagate in the workpiece 3 at the angle $\gamma_L \approx 70°$.

The longitudinal waves 11 are either the longitudinal waves which are received by the ultrasonic transducer array 60 and that were transmitted by the ultrasonic transducers 40 and 42 as the longitudinal waves 10 in FIG. 2 and reflected at a flaw 31a near the surface, or the longitudinal waves that were transmitted by the ultrasonic transducer array 60 and received as the longitudinal waves 10 after reflection from the flaw 31a by the ultrasonic transducers 40 and 42.

The ultrasonic transducer array 60, for transverse waves 12 with propagation directions of less than 60°, operates in the pulse echo mode. In other words, all of the ultrasonic transducer elements 61 are active as transmitters and receivers in alternation, and the transverse waves 12 reflected from flaws 31b, 31c are received by the ultrasonic transducer elements 61 of the ultrasonic transducer array 60 that have previously transmitted the transverse waves 12.

In the case of the longitudinal waves 11, the ultrasonic transducer array 60 operates in the transmit/receive mode, or in other words either only as a transmitter or only as a receiver. In this operating mode, the ultrasonic transducers 40 and 42 shown in FIG. 1 are then either active jointly or individually as receivers or as transmitters. This assures that the ultrasonic transducers operated as transmitters are acoustically and spatially separated from the ultrasonic transducers operated as receivers.

Instead of two ultrasonic transducers 40, 42 disposed next to the ultrasonic transducer array 60, in a simplified embodiment it is also possible for only a single ultrasonic transducer to be provided. In the configuration of two ultrasonic transducers 40 and 42, the lateral angular range for flaws near the surface that is detectable by the test head is enlarged.

Figure 4:
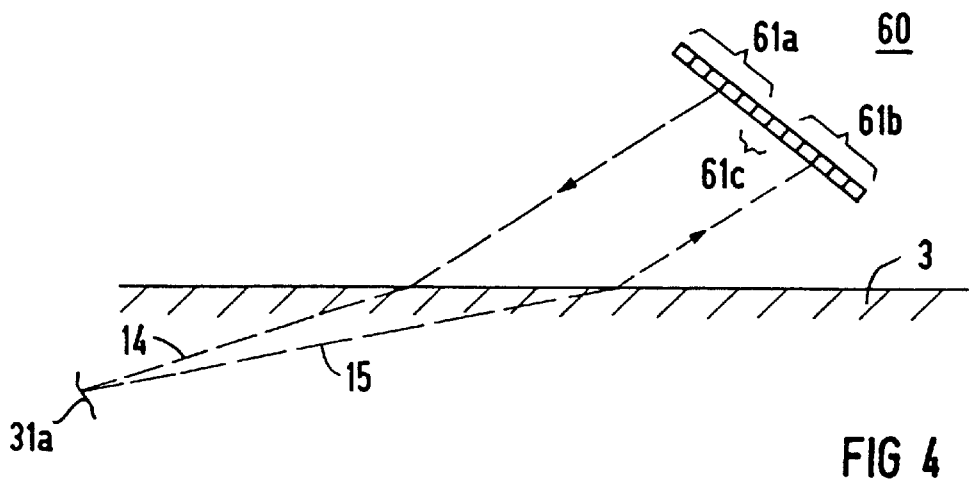
FIG. 4 is a sectional view illustrating an advantageous method for operating an ultrasonic transducer array disposed in the test head.

In an especially preferred embodiment, the ultrasonic transducer array 60 can also be operated, by suitable triggering of the ultrasonic transducer elements 61, in the transmit/receive mode for both longitudinal waves and for transverse waves. This is illustrated in FIG. 4 for longitudinal waves 14 and 15. To this end, the ultrasonic transducer array 60 is separated electronically, by suitable triggering, into two subgroups 61a and 61b. One of these subgroups, for instance the subgroup 61a, then functions as a transmitter, while the other subgroup 61b is active as a receiver. Preferably in this operating mode, the two subgroups 61a and 61b are separated by a subgroup 61c, which is switched to be inactive, in the middle of the array. It has been found in this operating mode that the acoustical decoupling attained thereby is sufficient to detect flaws 31a near the surface.

Figure 5:
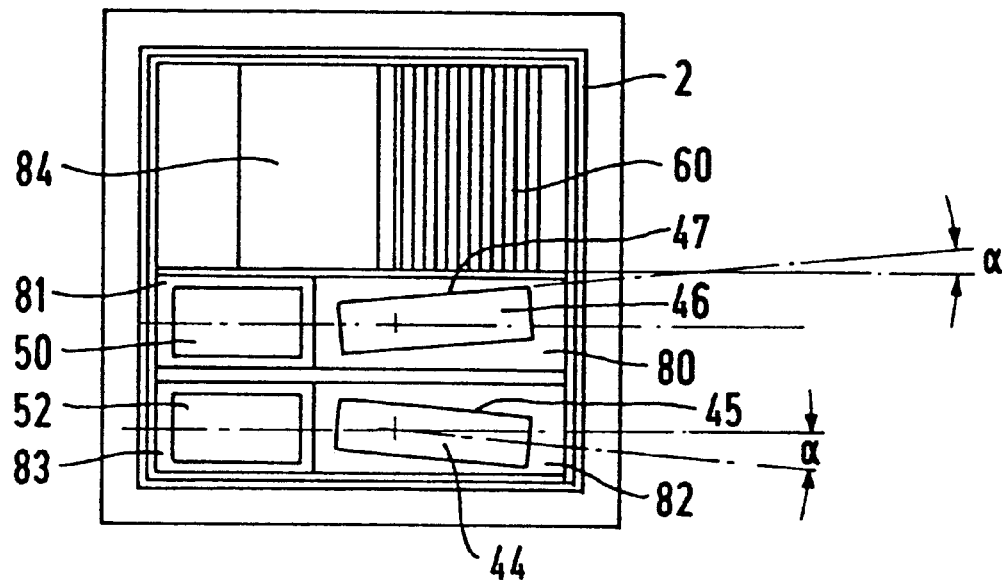
FIGS. 5 and 6 are respective plan and longitudinal sectional views showing a further advantageous embodiment of a test head according to the invention.
Figure 6:
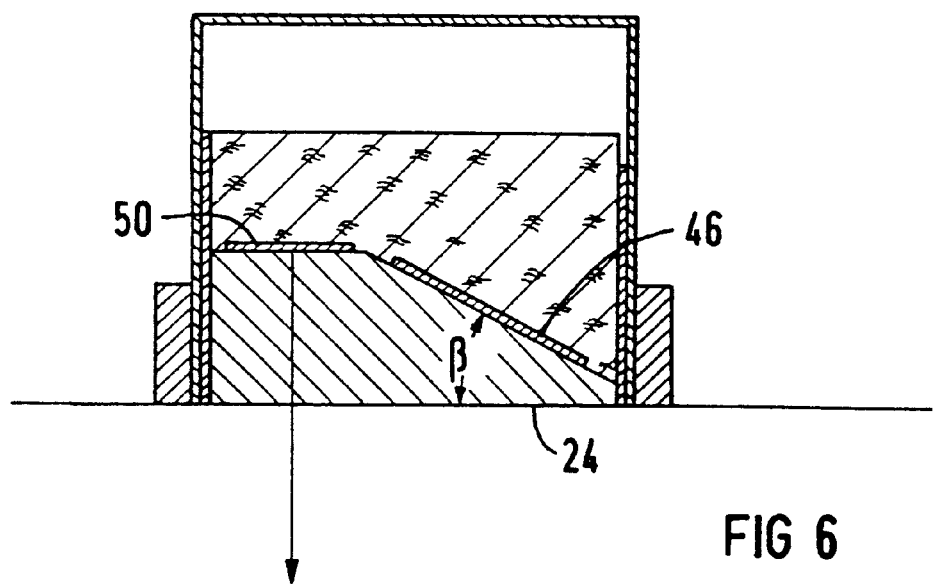

In the embodiment of FIGS. 5 and 6, two ultrasonic transducers 50 and 52, each being operated as transmitters and receivers, are provided in the housing 2 of the test head for a zero degree operation, or in other words for flaws disposed below the test head. As a result, the depth range and angular range detectable by this test head is increased as compared with the embodiment of FIGS. 1–4.

In this embodiment, two ultrasonic transducers 44, 46 that are disposed side by side are also provided for the 70° longitudinal wave mode. The ultrasonic transducer array 60 is also intended in this embodiment as a transmitter and receiver for transverse waves in the angular range between 45° and 60°, as well as a transmitter and receiver for longitudinal waves in the angular range of around 70°. The wedge angles with which the ultrasonic transducers 44, 46 and 60 are disposed on the delay bodies 80, 82 and 84 match the angles of the configuration of FIGS. 1–3. Only the angle of inclination a is reduced in this embodiment as compared with the embodiment of FIG. 1, in order to attain approximately the same lateral focal spacing for longitudinal waves. Additionally, in this embodiment the transmission and reception surfaces of the ultrasonic transducers 44 and 46 can be additionally inclined relative to one another by an apex angle.

Figure 7:
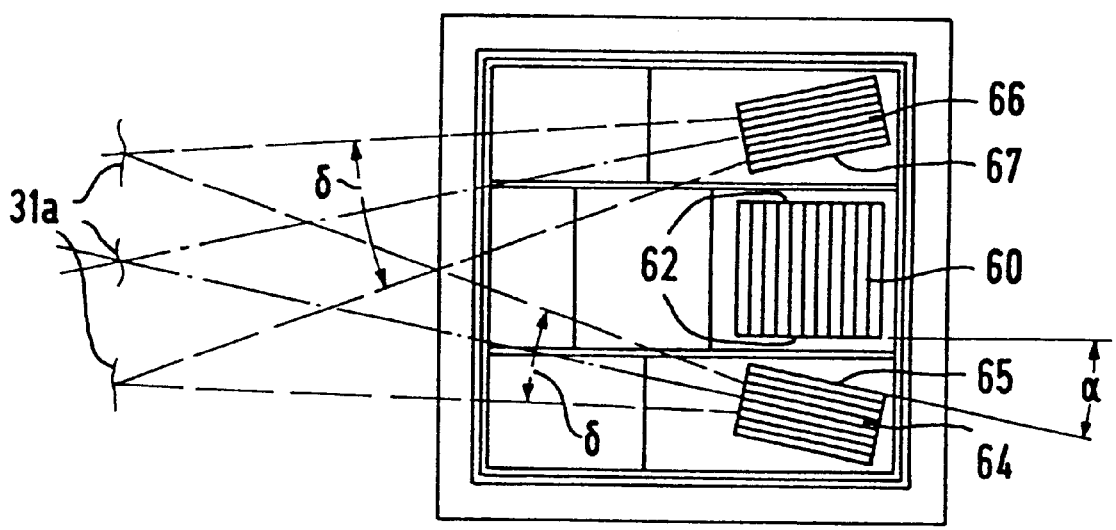
FIG. 7 is a plan view of an especially advantageous embodiment of an ultrasonic test head according to the invention, with three ultrasonic transducer arrays.

In the preferred embodiment of FIG. 7, the ultrasonic transducers 42 and 44 of FIGS. 1–3 are replaced by linear ultrasonic transducer arrays 64 and 66. In a preferred embodiment, the ultrasonic transducer arrays 64 and 66 each contain eight ultrasonic transducer elements 61. In this embodiment, the linear ultrasonic transducer arrays 64 and 66 are also disposed with respective long edges 65 and 67 thereof obliquely relative to the long edges 62 of the ultrasonic transducer array 60.

With these ultrasonic transducer arrays 64 and 66, the lateral transmission and/or reception angle $\delta$ for the longitudinal wave mode can be pivoted about an axis that is at right angles to the surface of the workpiece. This enlarges the lateral angular range in which flaws 31 near the surface can be detected. In this embodiment, the transducer configuration also operates for longitudinal waves in the transmission/reception mode, and all of the ultrasonic transducer arrays 60, 64 and 66 can be operated as both transmitters and receivers. In addition, the arrays can also be operated, as in FIG. 4, by electronic separation, even in the transmit/receive mode.

We claim:

1. An ultrasonic test head for ultrasonically testing flaws in a workpiece, comprising:
   a common housing;
   an ultrasonic transducer configuration disposed in said common housing; and
   at least one ultrasonic transducer array being disposed in said common housing for operation in a pulse echo mode for transverse waves propagating in a workpiece;
   said ultrasonic transducer configuration including at least two acoustically separate ultrasonic transducers to be operated in a transmit/receive mode for longitudinal waves propagating near a surface in the workpiece, said ultrasonic transducers being eccentrically disposed within said common housing.

2. The ultrasonic test head according to claim 1, wherein one of said ultrasonic transducers is operated as a transmitter and receiver for longitudinal waves, and said ultrasonic transducer array is disposed next to said one ultrasonic transducer.

3. The ultrasonic test head according to claim 2, wherein two of said ultrasonic transducers are operated as transmitters and receivers for longitudinal waves, and said ultrasonic transducer array is disposed between said two ultrasonic transducers.

4. The ultrasonic test head according to claim 2, wherein said ultrasonic transducer disposed next to said ultrasonic transducer array is an ultrasonic transducer array.

5. The ultrasonic test head according to claim 3, wherein said ultrasonic transducer disposed next to said ultrasonic transducer array is an ultrasonic transducer array.

6. The ultrasonic test head according to claim 1, wherein said ultrasonic transducer is disposed next to said ultrasonic transducer array, has a rectangular reception or transmission surface and has a long edge being disposed obliquely relative to a long edge of said ultrasonic transducer array.

7. The ultrasonic test head according to claim 2, wherein said ultrasonic transducer is disposed next to said ultrasonic transducer array, has a rectangular reception or transmission surface and has a long edge being disposed obliquely relative to a long edge of said ultrasonic transducer array, and said ultrasonic transducers disposed next to said ultrasonic transducer array have long edges forming an acute angle with one another.

8. The ultrasonic test head according to claim 6, including acoustically separate wedge-like delay bodies intersecting at wedge angles thereof, said ultrasonic transducer array and said at least one ultrasonic transducer being disposed on said delay bodies.

9. The ultrasonic test head according to claim 7, including acoustically separate wedge-like delay bodies intersecting at wedge angles thereof, said ultrasonic transducer array and said at least one ultrasonic transducer being disposed on said delay bodies.

10. The ultrasonic test head according to claim 8, wherein said delay bodies for said ultrasonic transducers have a segment parallel to a coupling surface for accommodating an additional ultrasonic transducer disposed parallel to said coupling surface.

11. A method for ultrasonically testing a workpiece, which comprises:

providing an ultrasonic test head having a common housing, an ultrasonic transducer configuration disposed in the common housing, and at least one ultrasonic transducer array being disposed in the common housing for operation in a pulse echo mode for transverse waves propagating in the workpiece, the ultrasonic transducer configuration including at least two acoustically separate ultrasonic transducers disposed eccentrically within the housing, said at least two ultrasonic transducers to be operated in a transmit/receive mode for longitudinal waves propagating near a surface in the workpiece, operating each of the at least one ultrasonic transducer array in a transmit/receive mode, operating the at least two longitudinal ultrasonic transducers in a transmit/receive mode, and determining the presence of flaws in the workpiece from signals output from the ultrasonic transducer array and the at least two longitudinal ultrasonic transducers.

12. The method according to claim 11, which comprises forming two subgroups being spatially separated from one another and having a plurality of ultrasonic transducer elements, in an ultrasonic transducer array operated in the transmit and receive mode.

13. The method according to claim 12, which comprises separating the subgroups from one another with another subgroup formed of inactive ultrasonic transducer elements.

* * * * *